United States Patent
Pisano et al.

(10) Patent No.: US 7,705,012 B2
(45) Date of Patent: Apr. 27, 2010

(54) CAMPTOTHECINS CONJUGATED IN POSITION 7 TO CYCLIC PEPTIDES AS CYTOSTATIC AGENTS

(75) Inventors: Claudio Pisano, Aprilia (IT); Giuseppe Giannini, Pomezia (IT); Maria Ornella Tinti, Rome (IT); Loredana Vesci, Rome (IT); Domenico Alloatti, Rome (IT); Sergio Penco, Milan (IT); Alma Dal Pozzo, Rome (IT); Ni Minghong, Milan (IT); Sabrina Dallavalle, Vimercate (IT); Lucio Merlini, Milan (IT); Franco Zunino, Milan (IT)

(73) Assignees: Sigma-Tau Industrie Farmaceutiche Riunite S.p.A., Rome (IT); Instituto Nazionale per lo Studio e la Cura Dei Tumori, Milan (IT)

( * ) Notice: Subject to any disclaimer, the term of this patent is extended or adjusted under 35 U.S.C. 154(b) by 737 days.

(21) Appl. No.: 11/596,015

(22) PCT Filed: May 4, 2005

(86) PCT No.: PCT/IT2005/000260

§ 371 (c)(1),
(2), (4) Date: Nov. 9, 2006

(87) PCT Pub. No.: WO2005/111063

PCT Pub. Date: Nov. 24, 2005

(65) Prior Publication Data

US 2008/0033003 A1   Feb. 7, 2008

(30) Foreign Application Priority Data

May 13, 2004   (IT) .................. RM2004A0240

(51) Int. Cl.
*A61K 31/4745* (2006.01)
*C07D 491/22* (2006.01)

(52) U.S. Cl. .................. 514/283; 546/48; 436/86; 514/2

(58) Field of Classification Search .......... 514/283, 514/2; 546/48; 436/86
See application file for complete search history.

(56) References Cited

U.S. PATENT DOCUMENTS 5,892,043 A   4/1999   Tsujihara et al.
6,242,457 B1   6/2001   Penco et al.

FOREIGN PATENT DOCUMENTS

| CN | 1300733 A | 6/2001 |
| CN | 1343209 A | 4/2002 |
| DE | 198 15 812 A1 | 10/1999 |
| EP | 0 781 781 A | 7/1997 |

OTHER PUBLICATIONS

Wermuth et al, "Stereoisomerism and Biological Activity . . .", J. Am. Chem. Soc. 1997, 119, 1328-1335.
International Search Report of PCT/IT2005/000260, mailed Aug. 25, 2005.
De Cesare et al; "Potent Antitumor Activity and Improved Pharmacological Profile of ST1481, a Novel 7-substituted Camptothecin", Cancer Research, vol. 61, 2001, pp. 7189-7195, XP002340217.
Arap et al; "Chemotherapy targeted to tumor vasculature", Current Opinion in Oncology, vol. 10, 1998, pp. 560-565, XP009052240.
Garcia-Carbonero, R. et al., "Current Perspectives on the Clinical Experience, Pharmacology, and Continued Development of the Camptothecins", Clinical Cancer Research, vol. 8, Mar. 2002, pp. 641-661.
Erdreich-Epstein, A., "Integrins vβ3 and Are Expressed by Endothelium of High-Risk Neuroblastoma and Their Inhibition Is Associated with Increased Endogenous Ceramide", Cancer Research 60, pp. 712-721, Feb. 2000.
Uhm, J., "Vitonectin, a Glioma-derived Extracellular Matrix Protein, Protects Tumor Cells from Apoptotic Death", Clinical Cancer Research, vol. 5, pp. 1587-1594, Jun. 1999.
Mizejewski, G. "Role of Integrins in Cancer: Survey of Expression Patterns", Integrins Expressions in Cancer, vol. 222, pp. 124-138, 1999.
Rader, C. et al., "Intergrin vβ3 targeted therapy for Kaposi's sarcoma with an in vitro evolved antibody", The FASEB Journal, vol. 16, pp. 2000-2002, Dec. 2002.

*Primary Examiner*—Charanjit S Aulakh
(74) *Attorney, Agent, or Firm*—Lucas & Mercanti, LLP

(57) ABSTRACT

Compounds of Formula (I) are described

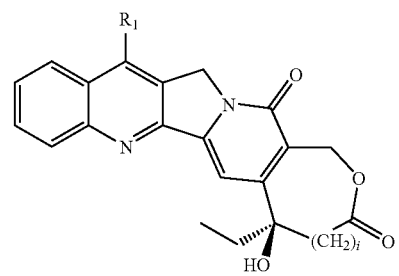

in which the $R_1$ group is as defined in the specification and includes the condensation of the camptothecin molecule in position 7 with a cyclopeptide containing the RGD sequence. Said compounds are endowed both with high affinity for integrin receptors $\alpha_v\beta_3$ and $\alpha_v\beta_5$ and with selective cytotoxic activity on human tumour cell lines at micromolar concentrations.

11 Claims, No Drawings

CAMPTOTHECINS CONJUGATED IN POSITION 7 TO CYCLIC PEPTIDES AS CYTOSTATIC AGENTS

This application is the U.S. national phase of international application PCT/IT2005/000260, filed 4 May 2005, which designated the U.S. and claims priority of IT RM2004A000240, filed 13 May 2004, the entire contents of each of which are hereby incorporated by reference.

FIELD OF THE INVENTION

The present invention relates to compounds with cytotoxic activity consisting of cyclopeptides containing the RGD sequence and derivatives of camptothecin, methods for the preparation thereof, their use as medicaments and compositions containing them.

In particular, the compounds described in the present invention are endowed both with high affinity for integrins $\alpha_v\beta_3$ and $\alpha_v\beta_5$ and selective cytotoxic activity on human cell lines at micromolar concentrations.

BACKGROUND TO THE INVENTION

Chemotherapeutic anticancer agents are the drugs with the most restrictive therapeutic window. In fact, since their cytotoxic activity is non-selective they may indiscriminately damage all the cells of the body with which they come into contact.

There currently exists the problem of directing the cytotoxic agent selectively against the tumour cells, allowing the agent to exert its activity without damaging the cells of the healthy surrounding tissues, or at least limiting the damage as much as possible.

It has been reported in the literature that blocking the integrins $\alpha_v\beta_3$ and $\alpha_v\beta_5$ by means of the use of selective cyclopeptides, the reference compound for which is regarded as cyclopentapeptide c(Arg-Gly-Asp-D-Phe-Val) (*JACS* 1997, 119, 1328-35; international patent application WO 97/06791), or by means of the use of monoclonal antibodies (*Cell*, 1994, 79, 1157-64) leads to the arrest of angiogenesis and to a reduction of tumour growth. In addition, antimetastatic effects have also been observed (*J. Clin. Invest.*, 1995, 96, 1815). Brooks et al. (*Science*, 1994, 264, 569-71) reported that the endothelial cells of the tumour vasculature and the tumour cells themselves preferentially express integrin $\alpha_v\beta_3$ compared to the quiescent cells of normal tissue. Among the compounds at an advanced stage of clinical development, we may mention c(Arg-Gly-Asp-D-Phe-MeVal), or EMD121974 or cilengitide.

Ruoslati and co-workers (*Current Opinion in Oncology*, 1998, 10, 560-5) showed that RGD analogues that bind to the tumour endothelium, once conjugated to the cytotoxic agent doxorubicin, form compounds that are more efficient and less toxic than doxorubicin alone. These authors also demonstrated, beyond any reasonable doubt, that the effect is attributable to the conjugation to RGD, inasmuch as the binding is antagonised by the free peptide itself (Arap, Pasqualini and Ruoslati, *Science*, 1998, 279, 377-380). Later, the same authors carried out other experiments consisting in chemically binding a pro-apoptotic peptide sequence to an RGD analogue, demonstrating that the new compounds were selectively toxic for angiogenic endothelial cells and had anticancer activity in mice (Ruoslati, *Nature Medicine*, 1999, 5, 1032-8).

Marcus et al., in international patent application WO 01/17563, describe specific anticancer activity for cytotoxic agents, such as camptothecin, conjugated by means of a spacer, consisting of one or more amino acids, to a non-peptidic inhibitor antagonist of integrins $\alpha_v\beta_3$ and $\alpha_v\beta_5$.

Aoki et al., *Cancer Gene Therapy*, 2001, 8, 783-787 describe the specific anticancer activity of a histidylated oligolysine conjugated to an RGD sequence, revealing a homing effect for tumours in mice.

The concept of binding at the cell surface mediated by integrins has been proposed for gene transport (Hart, et al., *J. Biol. Chem.*, 1994, 269, 12468-12474).

It has now been found that the 7-iminomethyl or 7-oxymethyl camptothecin derivatives conjugated, possibly by means of suitable spacers, to cyclopeptide derivatives containing the RGD sequence are endowed with high, selective anticancer activity and can be advantageously used for the preparation of medicaments for the treatment of tumours.

By virtue of their selective cytotoxic activity on tumour cells, the compounds according to the present invention yield medicaments with fewer and less severe side effects.

DESCRIPTION OF THE INVENTION

The object of the present invention are camptothecin derivatives conjugated to cyclopeptide derivatives containing the RGD sequence. The resulting molecules conserve unaltered both the cytotoxic properties of the original camptothecins and integrin binding properties with affinity comparable to that observed with the non-conjugated cyclopeptides. The result of this combination is to favour the concentration of the cytotoxic agent in those cells that most express integrins of the $\alpha_v\beta_3$ and $\alpha_v\beta_5$ type (homing). The cytotoxic agent exerts its intracellular activity in the conjugated and/or free form through enzymatic or hydrolytic action.

The object of the present invention are compounds of Formula (I)

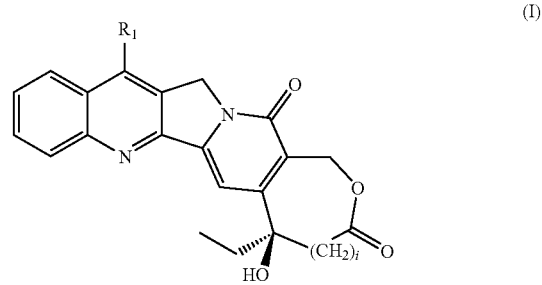

where:
i is 0 or 1;
$R_1$ is the group —CH=N—(O)$_m$—$R_2$—Z—X—Y;
where m is 0 or 1;
$R_2$ is selected from the group consisting of a linear or branched $C_1$-$C_7$ alkylene, linear or branched $C_2$-$C_7$ alkenylene, $C_3$-$C_{10}$ cycloalkylene, $C_3$-$C_{10}$ cycloalkenylene, $C_6$-$C_{14}$ arylene, arylene ($C_6$-$C_{14}$)-alkylene ($C_1$-$C_6$), alkylene ($C_1$-$C_6$)-arylene ($C_6$-$C_{14}$), aromatic or non-aromatic heterocycle ($C_3$-$C_{14}$), containing at least one heteroatom selected from the group consisting of O, N, S, heterocycloalkylene ($C_3$-$C_{10}$ containing at least one heteroatom selected from the group consisting of O, N, S)-alkylene ($C_1$-$C_6$), alkylene ($C_1$-$C_6$)-heterocycloalkylene ($C_3$-$C_{10}$ containing at least one heteroatom selected from the group consisting of O, N, S); a polyaminoalkyl group of formula —$(CH_2)_{m1}$—$NR_8$—$(CH_2)_{n1}$—$NR_9$—$(CH_2$—$CH_2$—$CH_2$—$NR_9)_{p1}$—H, where $m_1$ and $n_1$, which may be the same or different, are an integer number from 0 to 6;

$R_8$ and $R_9$, which may be the same or different, are selected from the group consisting of H, a linear or branched $C_1$-$C_6$ alkyl, Boc, Cbz; monosaccharides, such as 6-D-galactosyl, or 6-D-glucosyl; each of the above-mentioned groups may possibly be substituted by one or more groups selected from the group consisting of CN, $NO_2$, $NH_2$, OH, SH, COOH, COO-(alkyl)($C_1$-$C_5$), CONH-(alkyl)($C_1$-$C_5$), $SO_3H$, $SO_3$-(alkyl)($C_1$-$C_5$), where the alkyl group is linear or branched; a halogen atom;

Z is either absent, or is selected from —NH—, —CO—, —O—;

X is either absent, or is selected from the group consisting of —$COCHR_3NH$—, —$COCHR_6(CH_2)_{n2}R_4$—, —$R_4$—$CH_2(OCH_2CH_2)_{n3}OCH_2R_4$—, —$R_4(Q)R_4$—, —$R_5[Arg-NH(CH_2)_{n1}CO]_{n4}R_5$—, —$R_5$—[N-guanidinopropyl-Gly]$_{n3}R_5$—, —$CON[CH_2)_{n4}NHR_7]CH_2$—, in which $n_1$ is an integer number from 2 to 6, $n_2$ is an integer number from 0 to 5, $n_3$ is an integer number from 0 to 50, $n_4$ is an integer number from 2 to 7;

$R_3$ is H or linear or branched $C_1$-$C_4$ alkyl, optionally substituted with —COOH, —$CONH_2$, —$NH_2$ or —OH; $C_6$-$C_{14}$ aryl;

$R_4$ is selected from the group consisting of: —NH—, —CO—, —CONH—, —NHCO—;

$R_5$ is either absent or is —$R_4(Q)R_4$—;

$R_6$ is either a hydrogen atom, —$NH_2$;

$R_7$ is a hydrogen atom or linear or branched ($C_1$-$C_4$) alkyl;

Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$-$C_6$) alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

Y is the formula c(Arg-Gly-Asp-$AA_1$-$AA_2$), in which:

c means cyclic;

$AA_1$ is selected from the group consisting of: (D)-Phe, (D)-Trp, (D)-Tyr, (D)-2-naphthylAla, (D)-4-terbutyl-Phe, (D)-4,4'-biphenyl-Ala, (D)-4-$CF_3$-Phe, (D)-4-acetylamino-Phe;

$AA_2$ is selected from the group consisting of: NW—CH[$(CH_2)n_5$—CO]—CO, NW—CH[$(CH_2)_{n5}$—NH]—CO, NW-[4-$(CH_2)_{n5}$—CO]-Phe, NW-[4-$(CH_2)_{n5}$—NH]-Phe, [NW]-Gly, NW-Val, in which W is selected from H, linear or branched $C_1$-$C_6$ alkyl, —$(CH_2)_{n5}$—COOH where $n_5$ is an integer number from 0 to 5, 4-carboxybenzyl, 4-aminomethylbenzyl;

the $N_1$-oxides, racemic mixtures, their single enantiomers, their single diastereoisomers, the forms E and Z, mixtures thereof, the pharmaceutically acceptable salts.

The present invention also provides methods for the preparation of the above-mentioned compounds of Formula (I).

The present invention comprises the use of compounds with the above-mentioned general formula (I) as active ingredients for medicaments, and particularly for medicaments useful as topoisomerase I inhibitors. Among the therapeutic applications deriving from topoisomerase I inhibition, we mention tumours and parasitic or viral infections.

Given their particular pharmacological characteristics, the formula (I) compounds are also useful for the preparation of medicaments for the treatment of tumours and the metastatic forms thereof.

The present invention also comprises pharmaceutical compositions containing compounds of Formula (I) as active ingredients, in mixtures with at least one pharmaceutically acceptable vehicle and/or excipient.

The compounds according to the present invention are the result of the condensation of a camptothecin molecule, functionalised in position 7, with a cyclopeptide containing the Arg-Gly-Asp sequence. This structural combination has the advantage of favouring the concentration of the cytotoxic agent (camptothecin) in the cells that most express integrins of the $\alpha_v\beta_3$ and $\alpha_v\beta_5$ type. The cytotoxic agent exerts its activity in the conjugated and/or free form through enzymatic or hydrolytic action.

The definitions of the various functional groups and residues, as well as the definitions of the pharmaceutically acceptable salts that figure in the above-mentioned formula (I), are common knowledge to any expert chemist and no particular definitions are necessary. However, reference to such groups can be found in the technical and patent literature, e.g. in international patent applications WO 00/53607 (camptothecin derivatives having antitumor activity), WO 03/101995 (camptothecin with a modified lactone ring; i=1) and WO 03/101996 (ester in position 20 of camptothecin), filed in the name of the present applicant.

One initial group of preferred compounds consists of compounds of Formula (I) where m=1.

In this first group, $R_2$ is preferably alkylene, and more preferably methylene or ethylene, X is absent.

Another group of preferred compounds consists of compounds of Formula (I) in which X=$R_4CH_2(OCH_2CH_2)_{n3}OCH_2R_4$.

The most preferred compounds according to the present invention are the following:
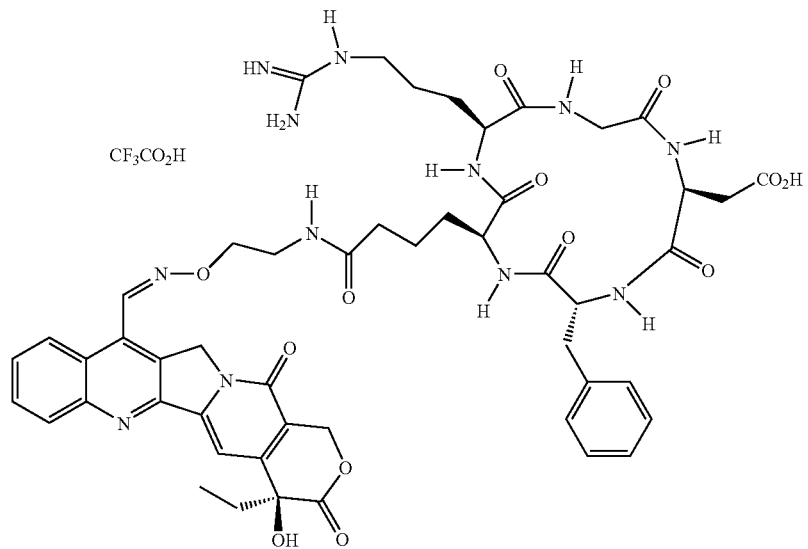
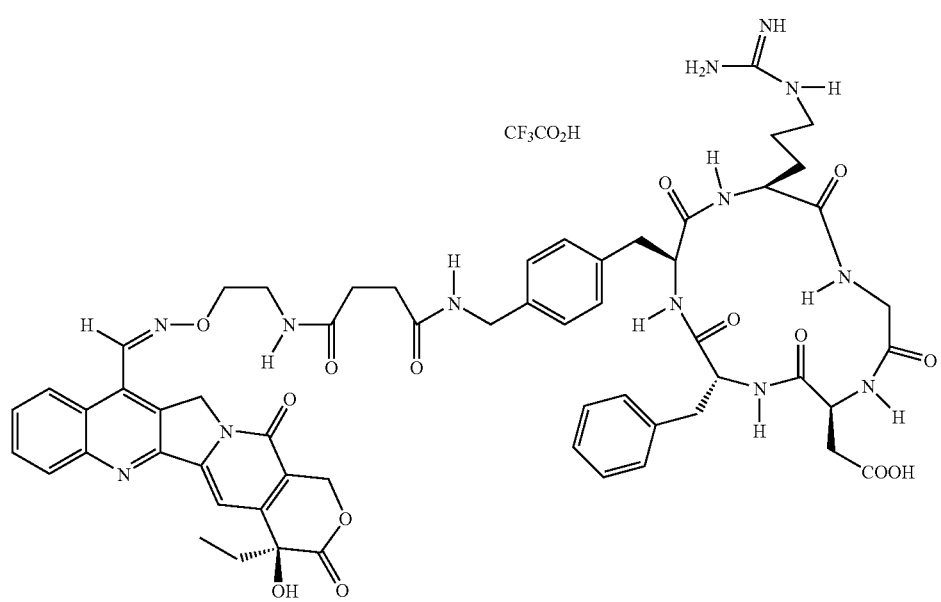

-continued

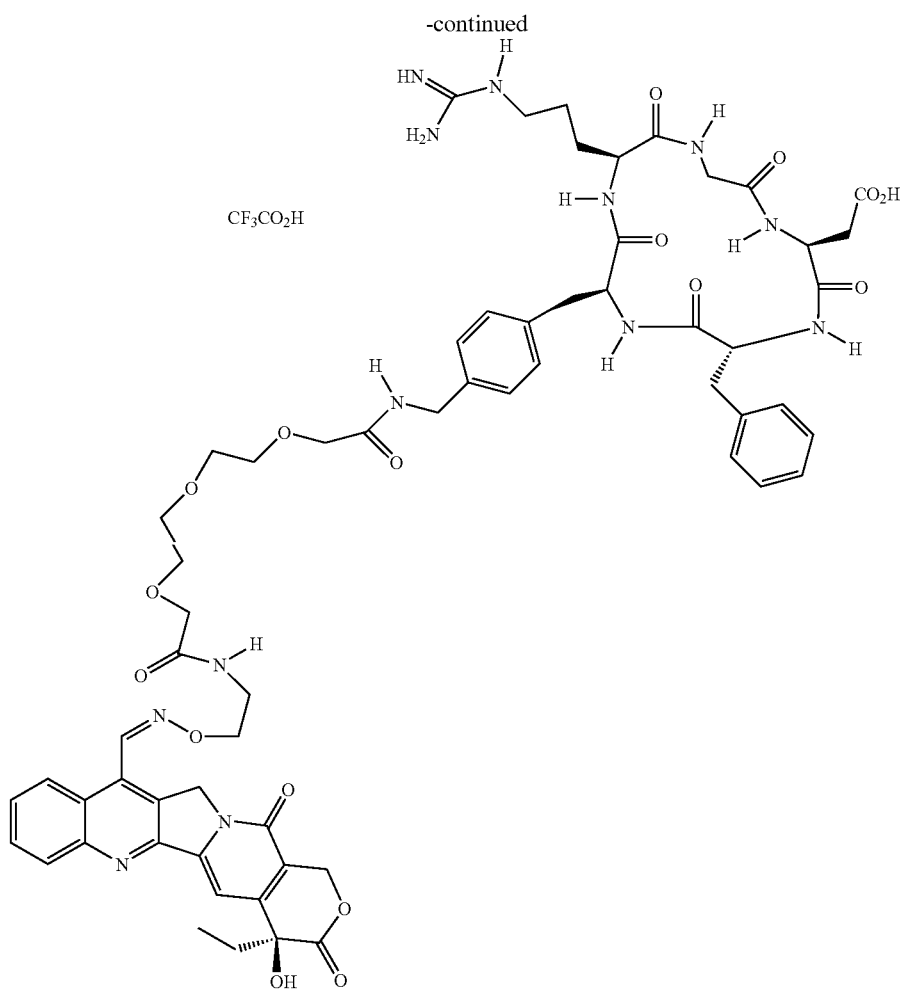

Compounds of Formula (I) can be prepared with the process described here below and exemplified for the preferred compounds according to the invention. This process constitutes a further object of the invention.

Fundamentally, the compounds of Formula (I) which are the object of the present invention are prepared by means of the condensation of camptothecin, the pentacyclic structure of which is indicated briefly here by the abbreviation CP, suitably functionalised in position 7, with a cyclopeptide derivative $Y_1$.

The condensation reaction can be schematically represented as follows:

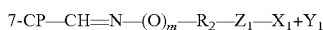

where 7-CP represents the polycyclic structure of a 7-substituted camptothecin and $Z_1$, $X_1$ and $Y_1$ represent respectively the groups Z, X and Y as defined in Formula I, eventually appropriately functionalised and/or protected so that the conjugated compounds of Formula I are obtained.

The 7-CP derivatives have been obtained using known approaches, such as those described in EP1044977, or in *J. Med. Chem.* 2001, 44, 3264-3274, S. Dallavalle et al., while the condensation reaction can be conducted using conventional methods, such as, for instance, *Journal of Controlled Release* 2003, 91, 61-73; S. S. Dharap et al.; *Journal of Medicinal Chem.* 2003, 46, 190-3, R. Bhatt;

The cyclopeptide $Y_1$ can be prepared according to conventional peptide synthesis techniques, as described in examples 1 to 6.

Once the desired cyclopeptide has been obtained, it will be used in the condensation reaction in its protected form, and the protective groups will be removed only after obtaining the final compound. The deprotection is carried out using known methods, e.g. acid conditions by means of the use of pure trifluoroacetic acid or in the presence of chlorinated organic solvents.

The camptothecin derivative 7-CP—CH=N—(O)$_m$—R$_2$—Z$_1$—X$_1$ is obtained using methods which are common knowledge to experts in the sector.

The key intermediate consists in amino(alkoxy)-iminomethyl-camptothecin, the preparation of which is described in WO 03/101995 and WO 03/101996, starting from 7-formyl-camptothecin by means of a reaction analogous to that described in the above-mentioned patent EP 1 044 977.

7-Formylcamptothecin is a known compound, the preparation of which is described in patent application WO 00/53607 and in the references cited therein, where, amongst other things, the preparation of the $N_1$-oxides is also described.

See also Dallavalle S., et al., *Bioorg. Med. Chem. Lett.*, 2001, 11(3): 291-4; Dallavalle S., et al., *J. Med. Chem.*, 2000, 43(21): 3963-9.

The Y(—COOH) compounds are new and constitute a further object of the present invention, particularly as intermediates for the preparation of the compounds of Formula (I).

The compounds described in the present invention are topoisomerase I inhibitors and are therefore useful as medicaments, particularly for the treatment of diseases that benefit from the inhibition of said topoisomerase. In particular, the compounds according to the present invention exhibit antiproliferative activity, and therefore are used for their therapeutic properties, and possess physicochemical properties which make them suitable for formulation in pharmaceutical compositions.

The pharmaceutical compositions contain at least one compound of Formula (I) as active ingredient, in an amount such as to produce a significant therapeutic effect. The compositions covered by the present invention are entirely conventional and are obtained using methods that are common practice in the pharmaceutical industry. According to the administration route opted for, the compositions will be in solid or liquid form and suitable for oral, parenteral or intravenous administration. The compositions according to the present invention contain, along with the active ingredient, at least one pharmaceutically acceptable vehicle or excipient. Formulation adjuvants, such as, for example, solubilising agents, dispersing agents, suspension agents or emulsifying agents may be particularly useful.

The compounds of Formula (I) can also be used in combination with other active ingredients, such as, for example, anticancer agents or other drugs with antiparasitic or antiviral activity, both in separate forms and in a single dosage form.

The compounds according to the present invention are useful as medicaments with anticancer activity, e.g. in non-microcytoma and small-cell lung cancer, or in colorectal or prostate cancer, glioblastoma and neuroblastoma, cervical cancer, ovarian cancer, gastrointestinal carcinoma, carcinoma of the liver, Kaposi's sarcoma, renal carcinoma, sarcoma and osteosarcoma, testicular carcinoma, carcinoma of the breast, carcinoma of the pancreas, melanoma, carcinoma of the urinary bladder and of the head and neck. One of the advantages afforded by the compounds according to the present invention is the combination of antitopoisomerase activity, proper to the camptothecin portion of the molecule, and the integrin inhibiting activity, provided by the cyclopeptide portion of the molecule. The result is the possible combined action of the compounds according to the present invention which will be favourably received in the oncological sector by the experts operating in that sector. In fact, the cyclopeptide portion, containing the Arg-Gly-Asp sequence, not only directs the molecule against tumours expressing integrins, but, once the target has been reached, is capable of exerting multiple functions, ranging from the internalisation of the cytotoxic portion of the molecule to integrin inhibiting activity, with the resulting advantages, particularly in terms of the inhibition of tumour angiogenesis. The cyclopeptide portion, once separated from the camptothecin portion, is also capable of exerting its action at a distance from the site of the tumour, and therefore the compounds according to the present invention also prove useful in the prevention or treatment of metastatic forms.

The medicaments which are the object of the present invention can also be used in the treatment of parasite diseases.

The following examples further illustrate the invention.

The abbreviations used are the following:

Aad (aminoadipic acid);
Amb (aminomethylbenzyl);
Amp (aminomethylphenylalanine);
Boc (ter-butoxycarbonyl);
CSA (camphosulfonic acid);
CTH (catalytic transfer hydrogenation);
DCC (dicyclohexylcarbodiimide);
DCM (dichloromethane);
DIEA (diisopropylethylamine);
DMF (dimethylformamide);
Fmoc (9-fluorenylmethyloxycarbonyl);
HOBT (hydroxybenzotriazole);
NMP (N-methyl-pyrrolidone);
Pht (phthaloyl);
Pmc (pentamethylchroman-6-sulphonyl);
ST1968 (2-aminoethoxyiminomethyl-camptothecin)
TBTU (tetrafluoroborate-O-benzotriazol-1-yl-tetramethyluronium);
TFA (trifluoroacetic acid).

EXAMPLE 1

Synthesis of c(Arg(Pmc)-Gly-Asp(OtBu)-D-Phe-Amp) (Protected ST2581)

1.587 mmol of Fmoc-Gly-Res (Res=Sasrin Resin®, Bachem) were suspended under stirring in 75 ml of DMF for 30 minutes, after which 18 ml of piperidine were added, continuing the stirring for a further 30 minutes. The resin, filtered and washed with DMF, was suspended in 50 ml of NMP (N-methyl-pyrrolidone) for 15 minutes, after which Fmoc-Arg(Pmc)-OH, HOBT, TBTU and DIEA were added (3.174 mmol of each); after 2 hours of stirring, the suspension was filtered and washed with DMF. After deprotection with piperidine, the coupling was repeated with the other amino acids in succession, operating each time as described above, namely: Fmoc-Amp(Cbz)-OH, Fmoc-D-Phe-OH, and Fmoc-Asp(OtBu)-OH. After the last deprotection of the Fmoc-N-terminal, the linear pentapeptide was released from the resin with 45 ml of 1% TFA in DCM. This was dissolved in approximately 1 l of $CH_3CN$, and 4.761 mmol of HOBT and TBTU and 10 ml of DIEA were added; the solution was kept under stirring for 30 minutes, the solvent was evaporated to a small volume and the precipitation of the product was completed with water. The filtered crude product was dissolved in 27 ml of a mixture of MeOH and DMF 1:1; 5 mmol of ammonium formiate and 0.55 g of 10% Pd/C were added and left under stirring at room temperature for 30 minutes. The suspension was filtered on celite and brought to dryness. The residue was purified by preparatory RP-HPLC (column: Alltima® C-18, Alltech; mobile phase 50% $CH_3CN$ in water+0.1% TFA; retention time (Rt)=9.13 minutes). 483 mg of a white powder were obtained.

$^1$H-NMR (DMSO-$d_6$) δ 8.3, 8.07, 8.04, 7.90, 7.80, 7.33, 7.15, 7.07, 4.62, 4.50, 4.35, 4.12, 4.01, 3.15, 3.03, 2.96-2.65, 2.58, 2.48, 2.32, 2.02, 1.75, 1.50, 1.35, 1.23.

Molecular mass (Maldi-Tof): 973

EXAMPLE 2

Synthesis of c(Ary(Pmc)-Gly-Asp(OtBu)-D-Phe-Aad) (Protected ST2650)

0.69 mmol of Fmoc-Gly-Res were treated exactly as described in example 1, with the difference that in this case the third and fourth amino acids were added in the form of dipeptide Fmoc-D-Phe-Aad(OBzl)-OH. After deprotection by means of CTH, and purification of the crude product with preparatory RP-HPLC (mobile phase: 66% $CH_3CN$ in water+0.1% TFA; Rt =17.29 minutes), 187 mg of pure peptide were obtained.

$^1$H-NMR (DMSO-d$_6$) δ 7.23, 4.58, 4.20-3.90, 3.28, 3.05, 2.99, 2.85, 2.74-2.35, 2.15, 2.05, 1.85-1.25.

Molecular mass (Maldi-Tof): 940

EXAMPLE 3

Synthesis of c(Arg(Pmc)-Gly-Asp(OtBu)-D-Phe-N-Me-Amp) (Protected ST2700)

To a suspension of Fmoc-Phe(4-Pht-N—CH$_2$)—COOH in anhydrous toluene brought to reflux 2 eq of CSA and 20 eq of paraformaldehyde were added, divided into 4 portions at intervals of 15 minutes. The mixture was left to cool, diluted with 120 ml of toluene and washed with 5% NaHCO$_3$ and water. After evaporation of the solvent, the residue was dissolved in 15 ml of CHCl$_3$+15 ml of TFA+700 µl of Et$_3$SiH; the mixture was left in the dark to stir for 42 hours. After evaporation of the solvent, the residue was purified by filtration on silica gel. Overall yield: 90%.

The linear peptide was synthesized in solid phase as described in example 1, inserting Fmoc-N-Me-Phe-(4-Pht-N—CH$_2$)—COOH as the third amino acid, prepared as described above. In this case the deprotections of N-Fmoc-terminal on resin were carried out with 30% diisopropylamine (300 eq) in solution in DMF (owing to the presence of phthalimide). After cyclisation, 500 mg of the peptide were dissolved hot in 10 ml of absolute EtOH, to which 0.9 ml of a solution of NH$_2$—NH$_2$.H$_2$O 1 M in ethanol was added. After heating at reflux for 2 hours, the solvent was evaporated and the residue taken up with 10 ml of DCM+10 ml of Na$_2$CO$_3$ solution under vigorous shaking. The crude final product was recovered from the organic phase after evaporation and purified by preparatory RP-HPLC (mobile phase: 52% CH$_3$CN in water+0.1% TFA; Rt=10 minutes).

$^1$H-NMR (CDCl$_3$) δ 8.29-7.66, 7.38-7.07, 4.95-4.77, 4.09, 3.41, 3.05-2.81, 2.51, 2.05, 1.74, 1.40, 1.26.

Molecular mass (Maldi-Tof): 987

EXAMPLE 4

Synthesis of c[Arg(Pmc)-Gly-As-p(OtBu)-D-Phe-Am-p(CO-(CH$_2$)$_2$—COOH)] (Protected ST2649)

120 mg of cyclopeptide c[Arg(Pmc)-Gly-Asp(OtBu)-D-Phe-Amp].TFA (prepared as described in example 1) were dissolved in 3.6 ml of a mixture of DCM-DMF 2:1, together with a stoichiometric amount of TEA and succinic anhydride. After 1 hour the reaction mixture was diluted with 30 ml of DCM and washed with water. The organic phase, dried and concentrated, yielded a residue of 100 mg of pure product.

Analytical RP-HPLC: column: Purosphere STAR®, Merck; mobile phase: 45% CH$_3$CN in water+0.1% TFA; Rt=13.17 minutes.

$^1$H-NMR(DMSO-d$_6$) δ 8.20-7.75, 7.19-7.02, 4.58, 4.45, 4.36, 4.30, 4.20, 4.05, 3.00, 2.97-2.57, 1.83, 1.62, 1.32.

Molecular mass (Maldi-Tof): 1073

EXAMPLE 5

Synthesis of c(Arg(Pmc)-Gly-As-p(OtBu)-D-Phe-N-Amb-GlW) (Protected ST2701)

To a solution of 1-22 mmol of Boc-monoprotected p-xylylenediamine in 6 ml of THF were added 1.83 mmol of TEA and, dropwise, a solution of 1.22 mmol of benzyl bromoacetate in 2 ml of THF. The mixture was left under stirring overnight, after which the solvent was evaporated and the residue purified on a flash column (CHCl$_3$-EtOAc, 9:1). 0.69 mmol of N-(4-Boc-NH-CH$_2$-benzyl)-glycine benzylester were obtained.

250 mg of Fmoc-D-Phe-OH were dissolved in 27 ml of DCM and 40 µl of diphosgene and 230 µl of sym-collidine were added; after 15 minutes 190 mg of the previously prepared ester were added, dissolved in 3 ml of DCM. After 3 hours, 80 µl of N-Me-piperazine were added to the reaction mixture and stirred for 10 minutes, after which the mixture was diluted with 10 ml of DCM and extraction was done with water, HCl 0.5N, water, 5% NaHCO$_3$ and water. After evaporation of the solvent, the residue was purified by flash chromatography on silica gel (DCM-EtOAc, 9:1). Yield: 80%.

To 100 mg of the product thus obtained, dissolved in 6 ml of MeOH, were added 76 µl of AcOH and 42 mg of HCOONH$_4$, and the mixture cooled to 0° C., and 50 mg of 10% Pd/C were added. After 30 minutes, the reaction mixture was filtered on celite. The filtrate was brought to dryness and purified on a flash column (CHCl$_3$-MeOH 9:1). Yield: 90%.

190 mg of the product thus obtained were dissolved in 1.2 ml of TFA and brought to dryness (deprotection of Boc); the residue was redissolved in 9 ml of 10% Na$_2$CO$_3$+6 ml of dioxane, cooled to 0° C. and a solution of 120 µl of benzyloxycarbonyl chloride diluted with 3 ml of dioxane was added dropwise. After 1 hour stirring at room temperature, evaporation was carried out under vacuum to a small volume, after which the mixture was diluted with water, the pH was reduced to 1 with HCl and extraction was done with EtOAc. After evaporation of the solvent, the residue was purified by filtration on silica gel, washing with CHCl$_3$-MeOH (8:2). Pure dipeptide yield: 82%.

0.69 mmol of Fmoc-Gly-Res were treated as described in example 1. After Arg, the previously prepared dipeptide Fmoc-D-Phe-N(4-Cbz-NH—CH$_2$-benzyl)-Gl was added in sequence. After deprotection of Cbz by means of CTH, the crude product c(Arg(Pmc)-Gly-Asp(OtBu)-D-Phe-N-Amp-Gly) was purified by preparatory RP-HPLC (mobile phase: 50% CH$_3$CN in water+0.1% TFA; Rt=10.5 minutes).

$^1$H-NMR (DMSO-d$_6$) δ 8.29-7.66, 7.44-6.90, 5.15, 4.72-4.18, 4.20, 4.05-3.32, 3.15, 3.06, 2.70, 2.51, 2.49, 2.01, 1.80-1.35, 1.49, 1.35, 1.23.

Molecular mass (Maldi-Tof): 973

EXAMPLE 6

Synthesis of c(Arg(Pmc)-Gly-As-p(OtBu)-D-Phe-Am-p(CO-CH$_2$—(OCH$_2$CH$_2$)$_n$—O—CH$_2$—COOH))

To a solution of 200 mg of c(Arg(Pmc)-Gly-Asp(OtBu)-D-Phe-Amp)-TFA (obtained as described in example 1) in 4 ml of a 3:1 DCM-DMF mixture was added a substantial excess of glycol diacid. DIEA (3 eq) and DCC (2 eq) were added to the same solution. The mixture was left under stirring overnight, after which it was diluted with DCM and washed with water.

The crude product was recovered by evaporating the organic phase and purified by flash chromatography (mobile phase: CHCl$_3$-MeOH 7:3+1% AcOH); the fractions containing the product were pooled, washed with water, dehydrated and brought to dryness, and yielded a residue of 157 mg of pure product.

Analytical RP-HPLC: (column: Purosphere STAR®, Merck; mobile phase: 50% CH$_3$CN 50% in water+0.1% TFA; Rt=10.96)

$^1$H-NMR (DMSO-d$_6$) δ 8.35-7.92, 7.20-7.00, 4.65, 4.50, 3.94, 3.60-3.45, 3.00-2.60, 2.55, 2.45, 2.30, 2.00, 1.70, 1.50, 1.30, 1.20.

Molecular mass (Maldi-Tof): corresponding to the different glycols used of various molecular weights.

Synthesis of Conjugated Derivatives

EXAMPLE 7 organic phases were washed with brine, anhydrified with Na$_2$SO$_4$, filtered and brought to dryness. 40 mg of crude product were obtained.

Chromatography: eluent CH$_2$Cl$_2$:CH$_3$OH=94:6→92:8. 11 mg of product are obtained.

Yield=61%

Release of Protective Groups 9 mg of protected product were dissolved in 4 ml of a CH$_2$Cl$_2$:CF$_3$COOH 1:1 solution and left to react at room temperature for 24 hours.

The reaction was monitored by TLC (CH$_2$Cl$_2$:CH$_3$OH=94:6).

The reacting solution was brought to dryness, obtaining a solid that was washed 3 times with Et$_2$O to eliminate the subproducts of the releasing reaction.

Synthesis of ST268

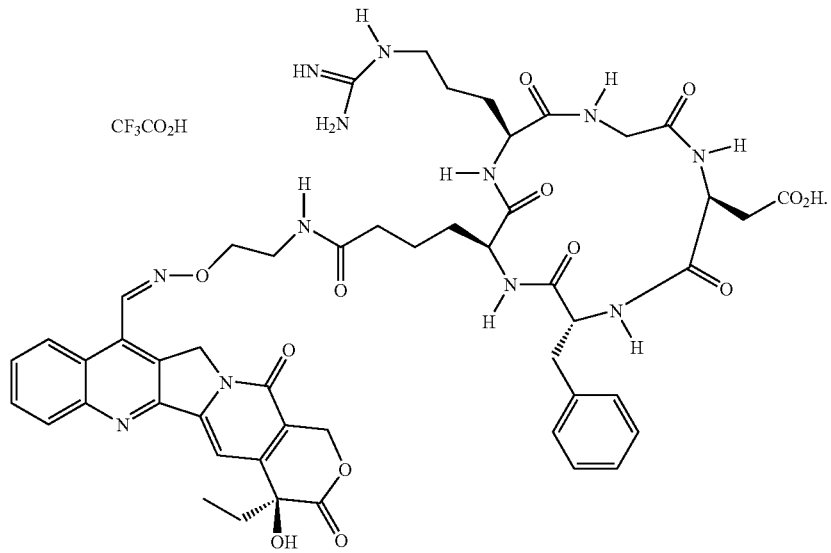

Condensation of ST1968 with Protected ST2650.

15 mg (0.016 mmoli) of protected ST2650 were dissolved in 1 ml of anhydrous DMF, and the solution brought to °0C.; 3.6 mg (0.027 mmol) of HOBt and 4 mg (0.019 mmol) of EDC were added and the mixture left to react for 30 minutes at 0° C.

6 mg of 2-aminoethoxyiminomethylcamptotecin (0.0131 mmoli) and 8 µl of DIEA (0.046 mmol) were then added and the mixture left to react at room temperature for approximately 60 hours. The reaction was monitored by TLC (CH$_2$Cl$_2$:CH$_3$OH=9:1).

The reaction mixture was diluted with H$_2$O (approximately 10 ml) and three extractions were done with CH$_2$Cl$_2$; the 5 mg of product were obtained in the form of trifluoroacetate.

Yield=66%.

Analytical Data:

R$_f$=0.24 in CH$_3$OH:H$_2$O=7:3 (TLC RP).

HPLC analysis: column: Dynamax® RP C$_{18}$, sample dissolved in methanol; flow rate: 1 ml/minute; eluent mixture: acetonitrile:water (0.1% TFA)=55:45; gradient: 10 minutes to 55% water (TFA 0.1%): 45% acetonitrile, 10 min to 10% water (TFA 0.1%), 10 min at 10% water (TFA 0.1%), 5 min to initial conditions. λ=360 nm 8.323 (25.8%); 10.969 (74.2%).
λ=254 nm 8.325 (29.4%); 10.975 (70.6%).

EXAMPLE 8

Synthesis of ST2724

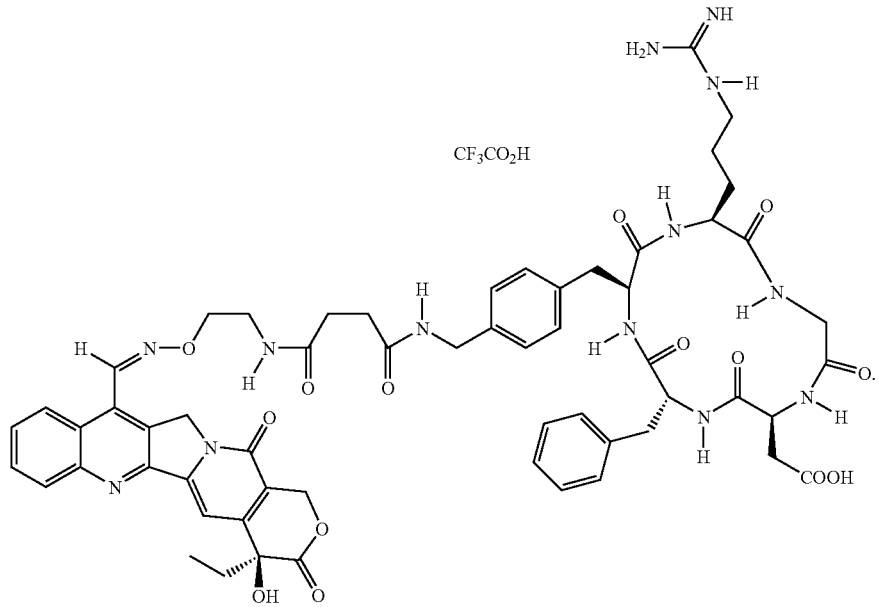

Condensation of ST1968 with Protected ST2649

25 mg (0.023 mmol) of protected ST2649 were dissolved in 2 ml of anhydrous DMF and the solution was brought to 0° C., after which 5 mg (0.039 mmol) of HOBt and 5 mg (0.027 mmol) of EDC were added and the mixture left to react for 30 minutes at 0° C.

8 mg of ST1968 (0.019 mmol) and 12 μl of DIEA (0.070 mmol) were added and the mixture left to react at room temperature for approximately 39 hours. The reaction was monitored by TLC ($CH_2Cl_2$:$CH_3OH$=9:1 to check the start).

The DMF was evaporated, the mixture was diluted with $H_2O$ (approximately 10 ml) and extraction was done 3 times with $CH_2Cl_2$. The organic phases were washed with brine, anhydrified with $Na_2SO_4$, filtered and brought to dryness. 29 mg of crude product were obtained.

Chromatography: eluent $CH_2Cl_2$:$CH_3OH$=94:6→9:1. 22 mg of product (lom184) consisting of the two sin and anti isomers of the CH=NO group bound in position 7 were obtained.

Yield=78%

HPLC-MS analysis: column: Symmetry $C_{18}$ (3.5 μm, 4.6× 75 mm); mobile phase: acetonitrile (TFA 0.1%): water (TFA 0.1%)=55:45; gradient: 10 minutes 55% water (TFA 0.1%): 45% acetonitrile, 10 min to 10% water (TFA 0.1%), 10 min at 10% water (TFA 0.1%), 5 min to initial conditions. λ=254 nm: $t_r$=5.20 (42%); $t_r$=5.97 (52%).

MS: (ESI) m/z=1492 corresponding to $[MH]^+$.

Removal of Protective Groups 22 mg of protected ST2724 were dissolved in 4 ml of a $CH_2Cl_2$:$CF_3COOH$ 1:1 solution and left to react at room temperature for 26 hours. The reaction was monitored by TLC (eluents: $CH_2Cl_2$:$CH_3OH$=95:5 to check the start; $H_2O$:$CH_3OH$=3:7 for the product).

Disappearance of protected ST2724 was also monitored by HPLC, injecting samples taken at t=0, t=2 hours, t=26 hours in the following gradient conditions: 10 minutes 55% water (TFA 0.1%): 45% $CH_3CN$, 10 min to 10% water (TFA 0.1%), 10 min at 10% water (TFA 0.1%), 5 min. to initial conditions; TrprotectedST2724=17.3; 18.1.

Column: Alltima RP $C_{18}$ (150 mm, DI 4.6 mm, 5μ). Sample dissolved in eluent mixture.

The reaction solution was brought to dryness and washed 3 times; the solid obtained was washed 3 times with $Et_2O$.

10 mg of trifluoroacetate product were obtained.
Yield=53%
$R_f$=0.52 in $CH_3OH$:$H_2O$=7:3 (TLC RP).
Melting point: dec. T>160° C.

HPLC analysis: column: Alltima RP $C_{18}$ (150 mm, DI 4.6 mm, 5μ). Sample dissolved in eluent mixture; mobile phase: acetonitrile (0.1% TFA): water (TFA 0.1%)=35:65; flow rate=1 ml/minute. Isocratic analysis. λ=254 nm 3.204

(15.0%); 3.982 (79.1%). λ=360 nm 3.204 (12.8%); 3.984 (83.9%).

EXAMPLE 9

Synthesis of ST2742

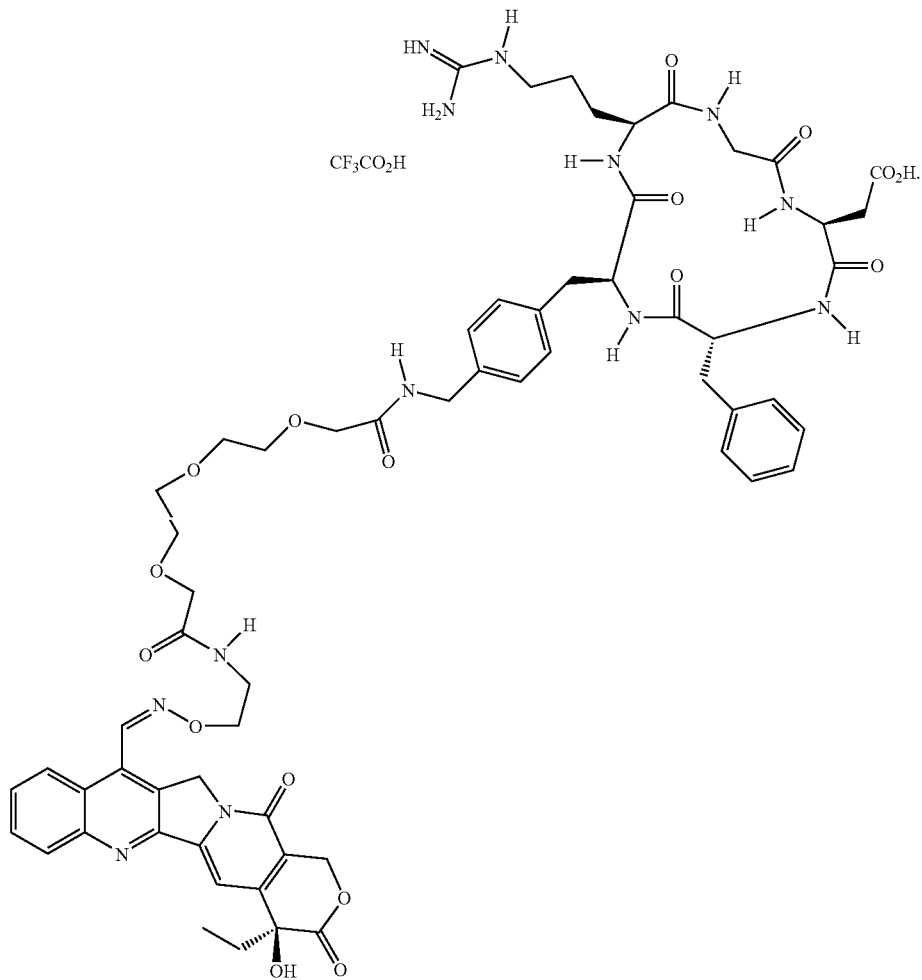

Condensation of ST1968 with Protected ST2661

110 mg (0.093 mmoli) of protected ST2661 were dissolved in 4 ml of anhydrous DMF, the solution was brought to 0° C., after which 21 mg (0.158 mmoli) of HOBt and 22 mg (0.112 mmol) of EDC were added, and the mixture left to react for 30 minutes at 0° C.

33 mg of ST1578 (0.077 mmol), 47 µl of DIEA (0.270 mmol) were added and the mixture left to react at room temperature for 24 hours. The reaction was monitored by TLC ($CH_2Cl_2:CH_3OH$=9:1 to check the start).

Processing: the DMF was evaporated, the mixture was diluted with $H_2O$ (approximately 15 ml) and three extractions were done with $CH_2Cl_2$. The organic phases were processed with brine, anhydrified with $Na_2SO_4$, filtered and brought to dryness. 166 mg of crude product were obtained.

Chromatography: eluent $CH_2Cl_2:CH_3OH$=95:5→8:2. 63 mg of product (Protected ST2742) were obtained. Yield=52%.

HPLC analysis: column: Alltima RP $C_{18}$ (150 mm, DI 4.6 mm, 5µ), sample dissolved in the eluent mixture; mobile phase: acetonitrile (TFA 0.1%): water (TFA 0.1%)=35:65; flow rate=1 ml/minute; gradient: 10 minutes to 55% water (TFA 0.1%): 45% acetonitrile, 10 min to 10% water (TFA 0.1%), 10 min at 10% water (TFA 0.1%), 5 min to initial conditions. λ=254 nm 15.17 (12.7%); 15.88 (80.2%). λ=360 nm 15.17 (17.5%); 15.88 (79.0%).

Removal of Protective groups 30 mg of protected ST2742 were dissolved in 4 ml of a $CH_2Cl_2:CF_3COOH$ 1:1 solution and left to react at room temperature for 25 hours. Disappearance of the protected product was monitored by HPLC, injecting samples taken at t=0, t=1 hour, t=2 hours, and t=24 hours in the analysis conditions described above.

19 mg of product consisting in the two sin and ainti isomers of the CH=NO group bound in position 7 were obtained.

Yield=73%; m.p. 160° C. (dec); MS (MALDI) m/z: 1272, 4.

$R_f$=0.44 in $CH_3OH:H_2O$=7:3 (TLC RP-18).

HPLC analysis: column: Alltima RP $C_{18}$ (150 mm, DI 4.6 mm, 5µ), sample dissolved in the eluent mixture; mobile phase: acetonitrile (TFA 0.1%): water (TFA 0.1%)=35:65;

flow rate=1 ml/minute; gradient: 85% water (TFA 0.1%): 15% acetonitrile, in 20' to 10% water (TFA 0.1%), 10' at 10% water (TFA 0.1%), in 5' to initial conditions. λ=254 nm 9.65 (28.4%); 10.24 (62.4%).

EXAMPLE 10

Biological Results

Binding to Integrin $\alpha_v\beta_3$ Receptors

The purified $\alpha_v\beta_3$ receptor (Chemicon, cat. CC1020) was diluted in buffer (20 mM Tris, pH 7.4, 150 mM NaCl, 2 mM $CaCl_2$, 1 mM $MgCl_2$, 1 mM $MnCl_2$) at a concentration of 0.5 µg/ml. An aliquot of 100 µl was added to 96-well plates and incubated overnight at +4° C. Plates were washed once with buffer (50 mM Tris, pH 7,4, 100 mM NaCl, 2 mM $CaCl_2$, 1 mM $MgCl_2$, 1 mM $MnCl_2$, 1% bovine serum albumin) and then incubated for another 2 hours at room temperature. Plates were washed twice with the same buffer and incubated for 3 hours at room temperature with the radioactive ligand [$^{125}$I]echistatin (Amersham Pharmacia Biotech) 0.05 nM in the presence of competition ligands. At the end of incubation, the wells were washed and the radioactivity determined using a gamma counter (Packard). Non-specific binding of the ligand was determined in the presence of excess cold echistatin (1 µM).

Binding to Integrin $\alpha_v\beta_5$ Receptors

The purified $\alpha_v\beta_5$ receptor (Chemicon, cat. CC1020) was diluted in buffer (20 mM Tris, pH 7.4, 150 mM NaCl, 2 mM $CaCl_2$, 1 mM $MgCl_2$, 1 mM $MnCl_2$) at a concentration of 1 µg/ml. An aliquot of 100 µl was added to 96-well plates and incubated overnight at +4° C. Plates were washed once with buffer (50 mM Tris, pH 7.4, 100 mM NaCl, 2 mM $CaCl_2$, 1 mM $MgCl_2$, 1 mM $MnCl_2$, 1% bovine serum albumin) and then incubated for another 2 hours at room temperature. Plates were washed twice with the same buffer and incubated for 3 hours at room temperature with the radioactive ligand [$^{125}$I]echistatin (Amersham Pharmacia Biotech) 0.15 nM in the presence of competition ligands. At the end of incubation, the wells were washed and the radioactivity determined using a gamma counter (Packard). Non-specific ligand binding was determined in the presence of excess cold echistatin (1 µM).

Evaluation of $IC_{50}$ Parameters

The affinity of the products for vitronectin receptors was expressed as $IC_{50}$ value ±SD, i.e. as the concentration capable of inhibiting 50% of the specific radioligand-receptor binding. The $IC_{50}$ parameter was elaborated using "ALLFIT" software.

Results

The conjugate ST2686 showed the most interesting affinity for integrin receptors compared with ST2724 and ST2742, given that the binding calculated as the $IC_{50}$ value was low (see Table 1). The ability of ST2686 to compete with the radioligand for the integrin $\alpha_v\beta_3$ receptors was greater than shown by the free RGD peptide ST2650 and comparable to that of ST2650 for the $\alpha_v\beta_5$ receptors (Table 2). Also ST2724 revealed a major affinity to integrin receptors compared with the free peptide ST2649 (Table 2), whereas ST2742 showed a minor affinity compared with the RGD free peptide ST2661, although it was a potent affinity for both integrin receptors.

Also the other RGD peptides (ST2581, ST2700, ST2701) demonstrated a potent interaction to integrin receptors (Table 2).

TABLE 1

Affinity of camptothecin-RGD conjugates for vitronectin $\alpha_v\beta_3$ and $\alpha_v\beta_5$ receptors

| Compound | $\alpha_v\beta_3$ | $\alpha_v\beta_5$ |
|---|---|---|
| | $IC_{50}$ ± SD (nM) | |
| ST2686 | 0.59 ± 0.01 | 0.37 ± 0.01 |
| ST2724 | 7.27 ± 0.06 | 8.39 ± 0.07 |
| ST2742 | 12.5 ± 2.1 | 6.5 ± 0.03 |

TABLE 2

Affinity of RGD peptides for vitronectin $\alpha_v\beta_3$ and $\alpha_v\beta_5$ receptors

| Compound | $\alpha_v\beta_3$ | $\alpha_v\beta_5$ |
|---|---|---|
| | $IC_{50}$ ± SD (nM) | |
| ST2650 | 28.6 ± 0.7 | 0.17 ± 0.01 |
| ST2649 | 37.6 ± 0.9 | 5.1 ± 0.07 |
| ST2661 | 4.0 ± 0.1 | 0.35 ± 0.09 |
| ST2581 | 1.7 ± 0.1 | 3.4 ± 0.1 |
| ST2700 | 7.2 ± 0.07 | 0.9 ± 0.005 |
| ST2701 | 36.7 ± 0.7 | 2.9 ± 0.1 |

Cytotoxicity of the Conjugates on Different Tumor Cell Lines

To evaluate the effect of the compound on cell survival, the sulphorodamine B test was used. PC3 human prostate carcinoma, A498 human renal carcinoma, A2780 human ovarian carcinoma cells were used. A2780 and PC3 tumor cells were grown RPMI 1640 containing 10% fetal bovine serum (GIBCO), whereas A498 tumor cells were grown in EMEM containing 10% fetal bovine serum (GIBCO).

Tumor cells were seeded in 96-well tissue culture plates (Corning) at approximately 10% of confluence and were allowed to attach and recover for at least 24 h. The effect of eight concentrations of the tested drugs were analyzed to calculate their $IC_{50}$ value (the concentration which inhibits the 50% of cell survival). The plates were incubated for 72 h at 37° C. At the end of the treatment, the plates were washed by remotion of the surnatant and addition of PBS 3 times. 200 µl PBS and 50 µl of cold 80% TCA were added. The plates were incubated on ice for at least 1 h. TCA was removed, the plates were washed 3 times for immersion in distilled-water and dried on paper and at 40° C. for 5 min. Then 200 µl of 0.4% sulphorodamine B in 1% acetic acid were added. The plates were incubated at room temperature for other 30 min. Sulphorodamine B was removed, the plates were washed for immersion in 1% acetic acid for 3 times, then they were dried on paper and at 40° C. for 5 min. Then 200 µl Tris 10 mM were added, the plates were kept under stirring for 20 min. The survival cell was determined as optical density by a Multiskan spectrofluorimeter at 540 nm. The amount of cells killed was calculated as the percentage decrease in sulphorodamine B binding compared with control cultures. The $IC_{50}$ values were calculated with the "ALLFIT" program.

As reported the conjugates showed the most potent cytotoxic activity on A2780 ovarian tumor cells with $IC_{50}$ values between 0.16 and 0.4 µM. On A498 tumor cells, ST2742 was more active with an $IC_{50}$ value of 0.74 µM followed by ST2686 and ST2724 ($IC_{50}$=3.2 and 4.3 µM, respectively) (Table 3).

TABLE 3

Cytotoxicity of the conjugates on PC3 prostate carcinoma, A498 renal carcinoma, A2780 ovarian carcinoma cells

| Compound | PC3 | A498 | A2780 |
|---|---|---|---|
|  | | $IC_{50} \pm SD, \mu M$ | |
| ST2686 | 15 ± 1.5 | 3.2 ± 0.4 | 0.4 ± 0.03 |
| ST2724 | 4.7 ± 0.4 | 4.3 ± 0.1 | 0.16 ± 0.001 |
| ST2742 | 27 ± 3.9 | 0.7 ± 0.1 | 0.18 ± 0.01 |

The invention claimed is:

1. Compounds of Formula (I)

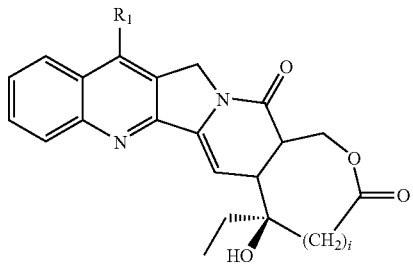

(I)

where:

i is 0 or 1;

$R_1$ is the group —CH=N—(O)$_m$—$R_2$—Z—X—Y;

where m is 0 or 1;

$R_2$ is selected from the group consisting of a linear or branched $C_1$-$C_7$ alkylene, linear or branched $C_2$-$C_7$ alkenylene, $C_3$-$C_{10}$ cycloalkylene, $C_3$-$C_{10}$ cycloalkenylene, $C_6$-$C_{14}$ arylene, arylene ($C_6$-$C_{14}$)-alkylene ($C_1$-$C_6$), alkylene ($C_1$-$C_6$)-arylene ($C_6$-$C_{14}$), aromatic or non-aromatic heterocycle ($C_3$-$C_{14}$), containing at least one heteroatom selected from the group consisting of O, N, S, heterocycloalkylene ($C_3$-$C_{10}$) alkylene ($C_1$-$C_6$) containing at least one heteroatom selected from the group consisting of O, N, S, alkylene ($C_1$-$C_6$)-heterocycloalkylene ($C_3$-$C_{10}$) containing at least one heteroatorm selected from the group consisting of O, N, S; a polyaminoalkyl group of formula —(CH$_2$)$_{m1}$—NR$_8$—(CH$_2$)$_{n1}$—NR$_9$—(CH$_2$—CH$_2$—CH$_2$—NR$_9$)$_{p1}$—H, where $m_1$ and $n_1$, which may be the same or different, are an integer number from 2 to 6 and $p_1$ is an integer number from 0 to 3;

$R_8$ and $R_9$, which may be the same or different, are selected from the group consisting of H, a linear or branched $C_1$-$C_6$ alkyl, Boc, Cbz; monosaccharides selected from the group consisting of 6-D-galactosyl, and 6-D-glucosyl; each of the above-mentioned groups may possibly be substituted by one or more groups selected from the group consisting of CN, NO$_2$, NH$_2$, OH, SH, COOH, COO-(alkyl)($C_1$-$C_5$), CONH-(alkyl)($C_1$-$C_5$), SO$_3$H, SO$_3$-(alkyl)($C_1$-$C_5$), where the alkyl group is linear or branched; a halogen atom;

Z is either absent, or is selected from —NH—, —CO—, —O—;

X is either absent, or is selected from the group consisting of —COCHR$_3$NH—, —COCHR$_6$(CH$_2$)$_{n2}$R$_4$—, —R$_4$—CH$_2$(OCH$_2$CH$_2$)$_{n3}$OCH$_2$R$_4$—, —R$_4$(Q)R$_4$—, —R$_5$[Arg-NH(CH$_2$)$_{n1}$CO]$_{n4}$R$_5$—, —R$_5$—[N-guanidinopropyl-Gly]$_{n3}$R$_5$—, —CON[(CH$_2$)$_{n4}$NHR$_7$]CH$_2$—, in which $n_1$ is an integer number from 2 to 6, $n_2$ is an integer number from 0 to 5, $n_3$ is an integer number from 0 to 50, $n_4$ is an integer number from 2 to 7;

$R_3$ is H or linear or branched $C_1$-$C_4$ alkyl, optionally substituted with —COOH, —CONH$_2$, —NH$_2$ or —OH; $C_6$-$C_{14}$ aryl;

$R_4$ is selected from the group consisting of: —NH—, —CO—, —CONH—, —NHCO—;

$R_5$ is either absent or is —R$_4$(Q)R$_4$—;

$R_6$ is either a hydrogen atom, —NH$_2$;

$R_7$ is a hydrogen atom or linear or branched ($C_1$-$C_4$) alkyl;

Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$-$C_6$), alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

Y is the formula c(Arg-Gly-Asp-AA$_1$-AA$_2$), in which:

c means cyclic;

AA$_1$ is selected from the group consisting of: (D)-Phe, (D)-Trp, (D)-Tyr, (D)-2-naphthylAla, (D)-4-terbutyl-Phe, (D)-4,4'-biphenyl-Ala, (D)-4-CF$_3$-Phe, (D)-4-acetylamine-Phe;

AA$_2$ is selected from the group consisting of: NW—CH[(CH$_2$)n$_5$—CO]—CO, NW—CH[(CH$_2$)n$_5$—NH]—CO, NW-[4-(CH$_2$)n$_5$—CO]-Phe, NW-[4-(CH$_2$)n$_5$—NH]-Phe, [NW]-Gly, NW-Val, in which W is selected from H, linear or branched $C_1$-$C_6$ alkyl, —(CH$_2$)n$_5$—COOH where n$_5$ is an integer number from 0 to 5,4-carboxybenzyl, 4-aminomethylbenzyl;

the N$_1$-oxides, racemic mixtures, their single enantiomers, their single diastereoisomers, the forms E and Z, mixtures thereof, the pharmaceutically acceptable salts.

2. Compounds according to claim 1, in which m is equal to 1.

3. Compounds according to claim 2, in which $R_2$ is alkylene and Z and X are absent.

4. Compounds according to claim 2, in which X=R$_4$CH$_2$(OCH$_2$CH$_2$)$_{n3}$OCH$_2$R$_4$.

5. Compound of formula
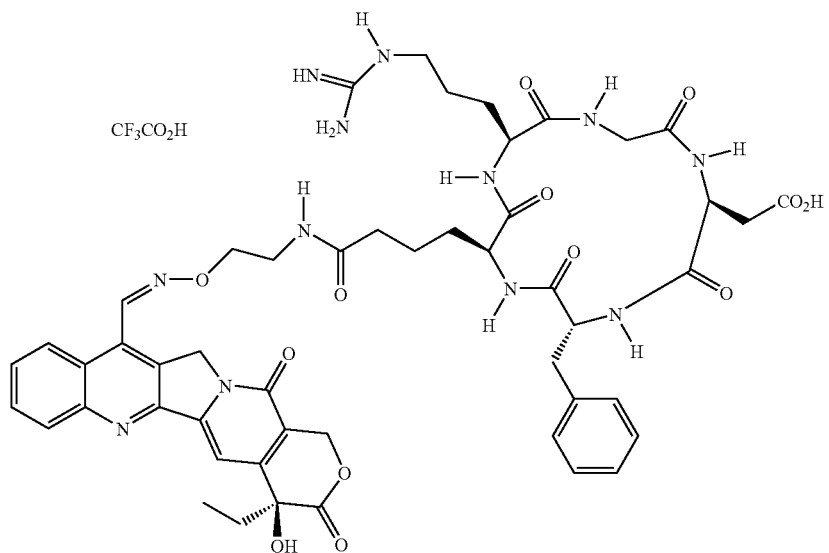
the $N_1$-oxides, racemic mixtures, their single enantiomers, their single diastereoisomers, the forms E and Z, mixtures thereof, the pharmaceutically acceptable salts.
6. Compound of formula
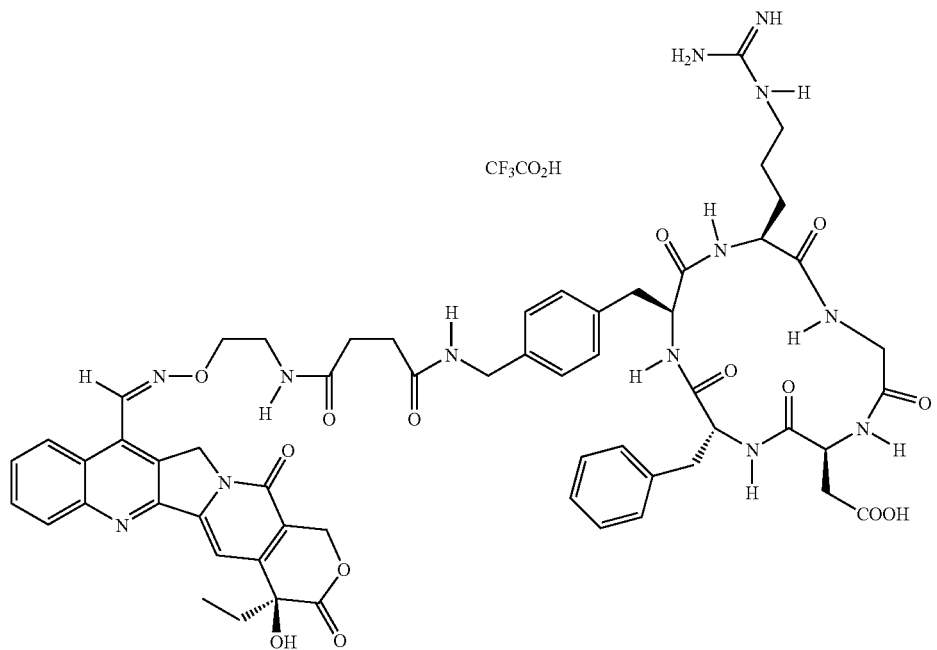

the $N_1$-oxides, racemic mixtures, their single enantiomers, their single diastereoisomers, the forms E and Z, mixtures thereof, the pharmaceutically acceptable salts.

7. Compound of formula

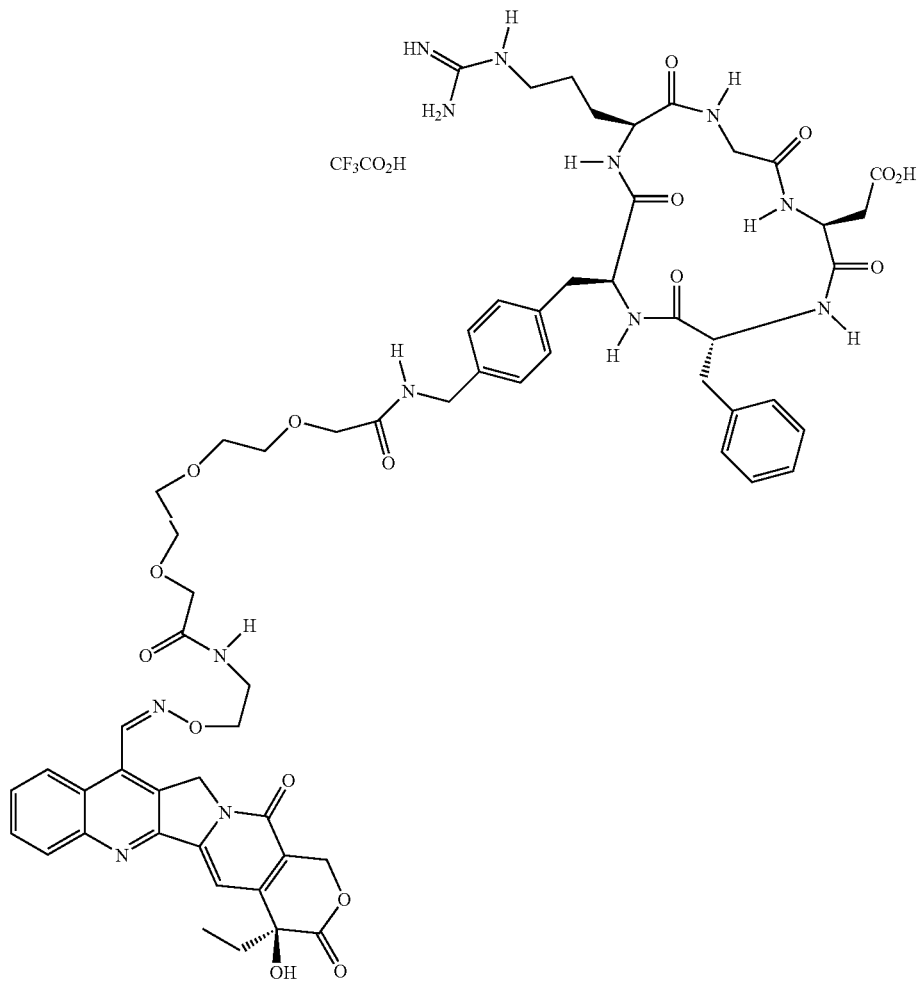

the $N_1$-oxides, racemic mixtures, their single enantiomers, their single diastereoisomers, the forms E and Z, mixtures thereof, the pharmaceutically acceptable salts.

8. Process for the preparation of the compounds of claim 1 wherein compounds of formula:

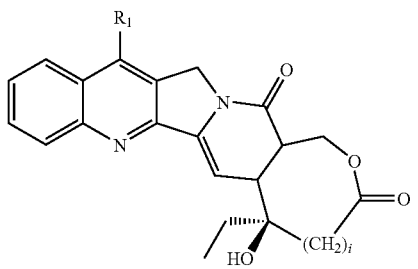

where:
i is 0 or 1;
$R_1$ is the group —CH═N—(O)$_m$—R$_2$—Z$_1$—X$_1$;
where m is 0 or 1;

$R_2$ is selected from the group consisting of a linear or branched $C_1$-$C_7$ alkylene, linear or branched $C_2$-$C_7$ alkenylene, $C_3$-$C_{10}$ cycloalkylene, $C_3$-$C_{10}$ cycloalkenylene, $C_6$-$C_{14}$ arylene, arylene ($C_6$-$C_{14}$)-alkylene ($C_1$-$C_6$), alkylene ($C_1$-$C_6$)-arylene ($C_6$-$C_{14}$), aromatic or non-aromatic heterocycle ($C_3$-$C_{14}$), containing at least one heteroatom selected from the group consisting of O, N, S; heterocycloalkylene ($C_3$-$C_{10}$) alkylene ($C_1$-$C_6$) containing at least one heteroatom selected from the group consisting of O, N, S, alkylene ($C_1$-$C_6$)-heterocycloalkylene ($C_3$-$C_{10}$) containing at least one heteroatom selected from the group consisting of O, N, S; a polyaminoalkyl group of formula —(CH$_2$)$_{m1}$—NR$_8$—(CH$_2$)$_{n1}$—NR$_9$—(CH$_2$—CH$_2$—CH$_2$—NR$_9$)$_{p1}$—H, where $m_1$ and $n_1$, which the same or different, are an integer number from 2 to 6 and $p_1$ is an integer number from 0 to 3;

$R_8$ and $R_9$, which may be the same or different, are selected from the group consisting of H, a linear or branched $C_1$-$C_6$ alkyl, Boc, Cbz; monosaccharides chosen from the group consisting of 6-D-galactosyl, or 6-D-glucosyl; each of the above-mentioned groups may possibly be substituted by one or more groups selected from the group consisting of CN, $NO_2$, $NH_2$, OH, SH, COOH, COO-(alkyl)($C_1$-$C_5$), CONH-(alkyl)($C_1$-$C_5$), $SO_3H$, $SO_3$-(alkyl)($C_1$-$C_5$), where the alkyl group is linear or branched: a halogen atom;

$Z_1$ is either absent, or is selected from —NH—, —CO—, —O— eventually functionalized and/or protected;

$X_1$ is either absent, or is selected from the group consisting of —COCHR$_3$NH—, —COCHR$_6$(CH$_2$)$_{n2}$R$_4$—, —R$_4$—CH$_2$(OCH$_2$CH$_2$)$_{n3}$OCH$_2$R$_4$—, —R$_4$(Q)R$_4$—, —R$_5$[Arg-NH(CH$_2$)$_{n1}$CO]$_{n4}$R$_5$—, —R$_5$—[N-guanidinopropyl-Gly]$_{n3}$R$_5$—, —CON[CH$_2$)$_{n4}$NHR$_7$]CH$_2$—, in which $n_1$ is an integer number from 2 to 6, $n_2$ is an integer number from 0 to 5, $n_3$ is an integer number from 0 to 50, $n_4$ is an integer number from 2 to 7; eventually functionalized and/or protected;

$R_3$ is H or linear or branched $C_1$-$C_4$ alky, optionally substituted with —COOH, —CONH$_2$, —NH$_2$ or —OH; $C_6$-$C_{14}$ aryl;

$R_4$ is selected from the group consisting of: —NH—, —CO—, —CONH—, —NHCO—;

$R_5$ is either absent or is —R$_4$(Q)R$_4$—;

$R_6$ is either a hydrogen atom, —NH$_2$;

$R_7$ is a hydrogen atom or linear or branched ($C_1$-$C_4$) alkyl;

Q is selected from the group consisting of: linear or branched $C_1$-$C_6$ alkylene; linear or branched $C_3$-$C_{10}$ cycloalkylene; linear or branched $C_2$-$C_6$ alkenylene; linear or branched $C_3$-$C_{10}$ cyclo-alkenylene; $C_6$-$C_{14}$ arylene; arylene ($C_6$-$C_{14}$)-alkylene; ($C_1$-$C_6$), alkylene ($C_1$-$C_6$)-arylene ($C_6$-$C_{14}$); aromatic or non-aromatic heterocyclyl ($C_3$-$C_{14}$), containing at least one heteroatom selected from the group consisting of O, N, S;

reacts with $Y_1$ wherein $Y_1$ is the formula c(Arg-Gly-Asp-AA$_1$-AA$_2$), eventually functionalized and/or protected; in which:

c means cyclic;

AA$_1$ is selected from the group consisting of: (D)-Phe, (D)-Trp, (D)-Tyr, (D)-2-naphthylAla, (D)-4-terbutyl-Phe, (D)-4,4'-biphenyl-Ala, (D)-4-CF$_3$-Phe, (D)-4-acetylamine-Phe;

AA$_2$ is selected from the group consisting of: NW—CH [(CH$_2$)n$_5$ —CO]—CO, NW—CH[(CH$_2$)n$_5$—NH]—CO, NW-[4-(CH$_2$)n$_5$—CO]-Phe, NW-[4-(CH$_2$)n$_5$—NH]-Phe, [NW]-Gly, NW-Val, in which W is selected from H, linear or branched $C_1$-$C_6$ alkyl, —(CH$_2$)n$_5$—COOH where n$_5$ is an integer number from 0 to 5,4-carboxybenzyl and 4-aminomethylbenzyl.

9. Pharmaceutical composition containing at least one compound according to claim 1 as the active ingredient in a mixture with at least one pharmaceutically acceptable excipient and/or vehicle.

10. A method for the treatment of prostate cancer, ovarian carcinoma and renal carcinoma.

11. Method according to claim 10 wherein prostate cancer, ovarian carcinoma and renal carcinoma are metastatic forms.

* * * * *